United States Patent [19]

Zwicker et al.

[11] 4,178,796
[45] Dec. 18, 1979

[54] METHOD AND APPARATUS FOR PARTICLE SIZE ANALYSIS

[75] Inventors: James D. Zwicker; Ghyslain Dube, both of Arvida, Canada

[73] Assignee: Alcan Research and Development Limited, Montreal, Canada

[21] Appl. No.: 902,689

[22] Filed: May 4, 1978

[30] Foreign Application Priority Data

May 9, 1977 [GB] United Kingdom ............... 19433/77

[51] Int. Cl.² ........................................... G01N 15/04
[52] U.S. Cl. ................................. 73/61.4; 73/432 PS
[58] Field of Search ........................ 73/432 PS, 61.4

[56] References Cited

U.S. PATENT DOCUMENTS

| 3,572,930 | 3/1971 | Morcom et al. | 73/61.4 X |
| 3,812,966 | 5/1974 | Beach et al. | 73/432 PS X |

*Primary Examiner*—Gerald Goldberg
*Assistant Examiner*—Joseph W. Roskos

*Attorney, Agent, or Firm*—Cooper, Dunham, Clark, Griffin & Moran

[57] ABSTRACT

An on-line particle size analyzer which is able to take measurements on material flowing along a line in real time and thus enable automatic process controls to be effected. The apparatus periodically takes a sample of material, dilutes it to a predetermined concentration in a turbidimeter, and then passes it to one of a number of vertical sedimentation cells in which a particle size analysis is carried out. Each sedimentation cell is formed simply as an enlarged part of a line passing from the turbidimeter around a loop back to the turbidimeter and, in order to fill the respective sedimentation cell, the sample is pumped round the loop until steady-state conditions have been reached, whereupon the flow is stopped and measurements begun. When the measurements, which are carried out by optical means, are completed, the whole loop, including the sedimentation cell is automatically flushed out. A central control unit controls the sequence of operations, and enables virtually continuous monitoring of the material flowing down the line.

24 Claims, 6 Drawing Figures

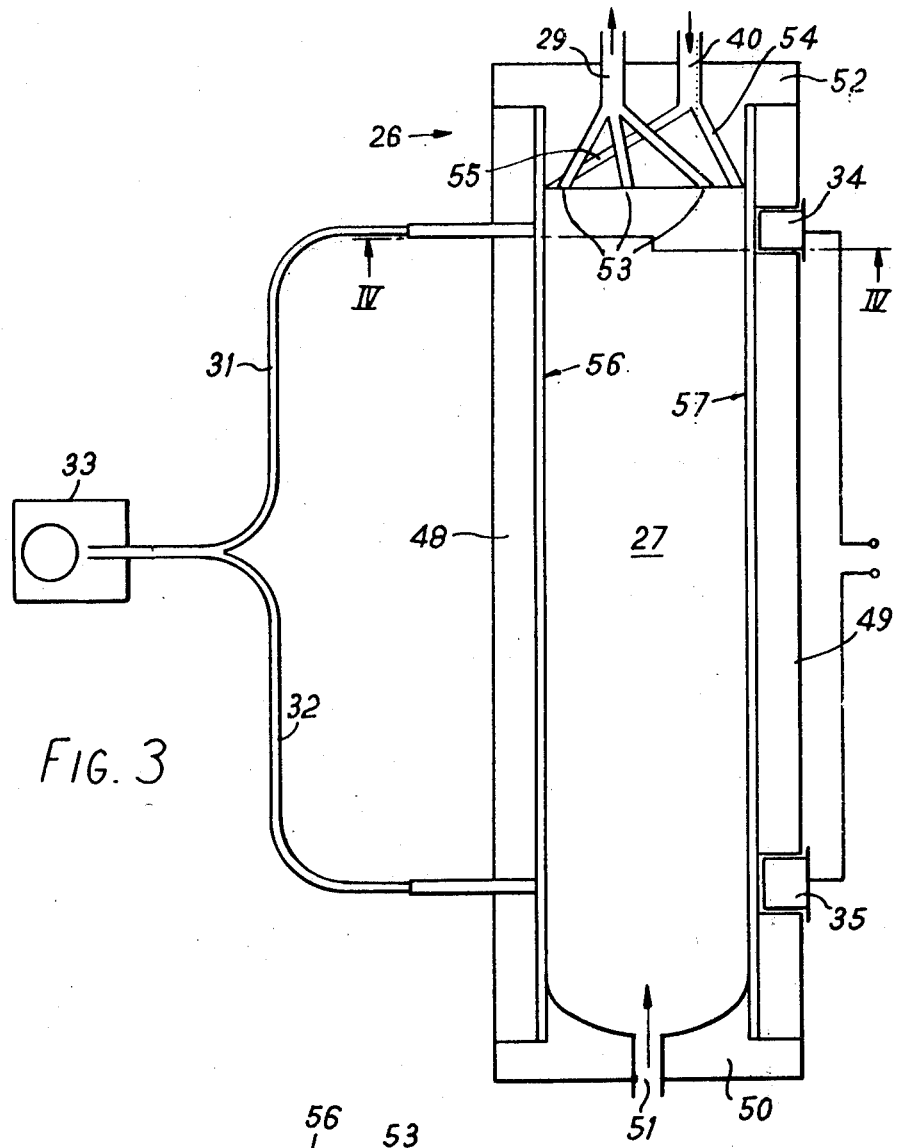
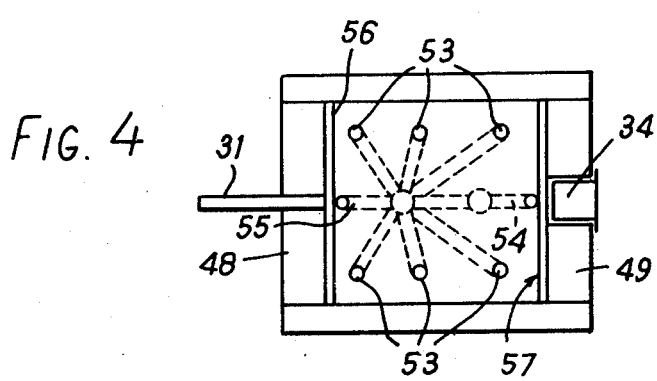

METHOD AND APPARATUS FOR PARTICLE SIZE ANALYSIS

This invention relates to a particle size analyser, to a method of effecting particle size analysis, and to a sedimentation cell for use in such analysis.

It is becoming increasingly apparent that the physical properties of powders significantly affect the quality of many products. In particular, information concerning the average particle size, the particle size distribution, and the surface area of powders is necessary for a full understanding of the complex nature of many chemical processes and the behaviour of their associated equipment.

Various techniques have been adopted for obtaining the necessary information and one of these, the sedimentation rate technique, forms the basis of the present invention. The sedimentation rate technique utilizes the fact that the velocity of a particle falling through a viscous medium under gravity is mathematically related to the diameter of the particle by the formula:-

$$D = K v^{\frac{1}{2}}$$

where
D is the diameter of the particle;
v is the velocity of fall of the particle;
and
K is a constant.

In the above formula, known as Stokes law, the constant K is given by:

$$K = \left( \frac{18\eta}{(\rho - \rho_o) g} \right)^{\frac{1}{2}}$$

where
g is the acceleration due to gravity;
$\rho$ is the density of the particle;
$\rho_o$ is the density of the viscous medium;
and
$\eta$ is the viscosity of the viscous medium.

Stokes Law is limited to the laminar flow region but its application may be extended somewhat by the use of mathematical manipulations of the data.

The analysis is carried out by allowing the material to be tested to settle in a container, known as a sedimentation cell, time being measured from the beginning of the settling period. The manner in which the particles settle is monitored and, from the information thus obtained, the average particle size, the particle size distribution, and the surface area of the powder can be ascertained.

According to a first aspect of the invention, there is provided a particle size analyser comprising a sequential sampler for periodically collecting a sample of a material to be analysed flowing along a line, a mixing tank for separately and sequentially receiving said samples, said mixing tank having means for automatically diluting each sample to a predetermined concentration, a sedimentation cell in which analysis of each individual sample by sedimentation is performed, a pump for separately and successively transferring each diluted sample from the mixing tank to the sedimentation cell, and means for draining each sample from the sedimentation cell when the analysis of that sample is complete.

According to a second aspect of the invention there is provided a method of automatically effecting particle size analysis on material flowing along a line, said method comprising the steps of periodically collecting a sample of the material to be analysed, separately and sequentially diluting each said sample to a predetermined concentration, passing each diluted sample to a sedimentation cell in which a sedimentation analysis of the sample is performed, and draining each sample when its analysis is complete, and wherein the period between the collection of each successive sample is never shorter than the sedimentation analysis time for the sample.

The material to be analysed may take the form of either solid particles in a liquid carrier, or solid particles in dry powder from. In both cases the sample, once introduced into the mixing tank, is diluted automatically to a predetermined concentration by the addition of an appropriate liquid, for example water. Preferably means are provided for holding the resultant slurry in suspension by mechanical agitation. This may be achieved by mechanical means, such as a stirrer, or ultrasonic means, or a combination of both mechanical and ultrasonic means, the choice being made by consideration of the fragility of the particles in the slurry.

Since the longest part of the analysis is the sedimentation process itself, which takes place in the sedimentation cell, it is preferred to provide more than one sedimentation cell linked to a single mixing tank, each cell being supplied by means of its own pump. In one system, for example, the use of two sedimentation cells has enabled at least twelve analyses per hour to be carried out.

Preferably means are also provided for automatically flushing out the sedimentation cell between each sedimentation analysis to clean out any particles remaining from the previous analysis.

Preferably the sedimentation cell comprises a sealed light-tight vessel in which the analysis by sedimentation is carried out, means for introducing a slurry to be analysed into the vessel, a plurality of spaced light emitters arranged along the side of vessel and operable to direct light through the interior of the vessel, and for each light emitter, a corresponding light detector arranged to receive light from its light emitter through the interior of the vessel.

The light emitter may be any optical source, such as a tungsten lamp, which is equipped with suitable filters to give an output within the range from infra-red to ultra-violet, or a laser source. The choice of light emitter depends on the nature of the slurry being analysed. It goes without saying that the light detectors should be such that they respond to the frequency of the light source, and preferably they are matched to only that frequency.

The number of light emitters, and their associated detectors, which are required depends upon the precision required, although two emitters, one near the top of the vessel and one near the bottom, have been found sufficient for most purposes. Preferably a common light source is used for all the light emitters, light being taken to the side of the vessel by suitable light guides, for example fibre optics. An additional one of such light guides may be provided, which additional light guide passes light directly to an additional light detector to permit compensation for fluctuations in light intensity.

By an appropriate choice of settling medium and number and position of light emitters/detectors in the sedimentation cell, a complete size distribution curve and specific surface area may be obtained within, for example three to five minutes, provided that an on-line computer is available for recording and calculation of data. Many earlier on-line analysers are capable of providing only one or, at best, a few points on the size distribution curve, whereas the instrument of this invention is able to provide a complete size distribution curve.

The means for introducing the slurry into the vessel may comprise a common inlet/outlet pipe, the slurry being pumped into and out of the vessel through this pipe. However, in an embodiment of the invention, separate inlet and outlet pipes are used, a "flow-through" system being used to introduce slurry into the vessel for analysis. In the flowthrough system, slurry at the correct concentration is pumped in a closed loop from the mixing tank through the vessel, and back into the mixing tank again. The flow is continued for a time sufficient to ensure that steady state conditions have been reached, whereupon the flow is stopped and the sedimentation analysis commenced. The purpose of this system is to ensure that a representative portion of the diluted sample is in the vessel for analysis, and it is important to ensure that the flow is at a sufficient rate to ensure that premature settling of the particles does not occur.

The sedimentation vessel itself is normally tall and fairly narrow. Its horizontal cross section may be circular, or any other suitable shape, but in an embodimeand of the invention the cross section of the vessel is rectangular, since this has been found to improve the optical properties of the cell.

In order that the invention may be better understood several embodiments thereof will now be described by way of example only and with reference to the accompanying drawings in which:-

FIG. 3 is a diagrammatic side view of a sedimentation cell for use with the particle size analyser of this invention;

FIG. 4 is a section along the lines IV—IV of FIG. 3;

Figure 1:
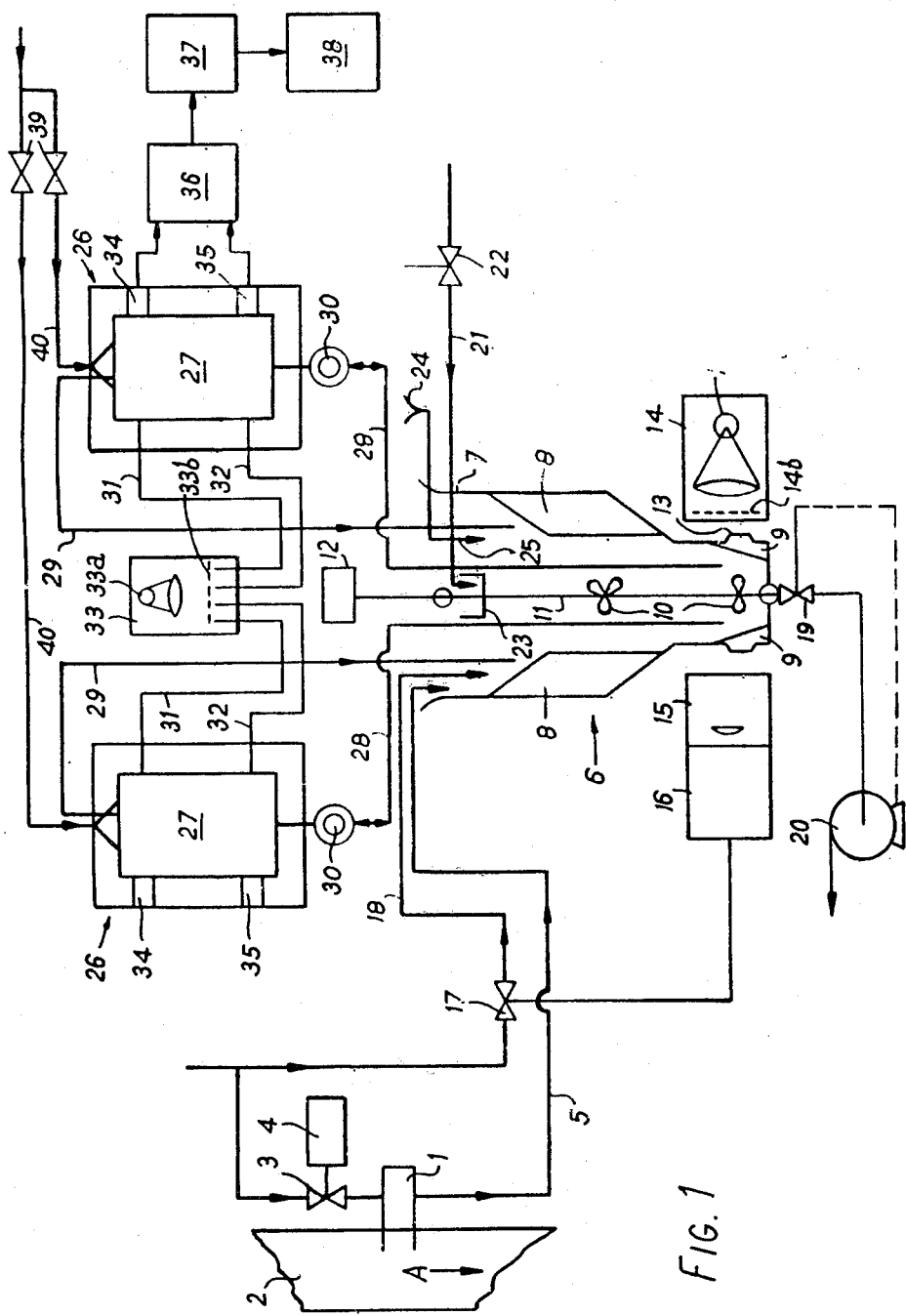
FIG. 1 is a schematic diagram of the particle size analyser of the present invention.

Referring to FIG. 1, the analyser comprises a plunger-type sampler 1 which is operable to periodically withdraw a sample of material to be analysed as it flows along a pipe 2 in the direction of arrow A. The sample is flushed out of the sampler 1 by means of a flow of suitable liquid, for example water, controlled by a valve 3, which valve is itself controlled by an automatic sample controller 4. The sample thus passes into a line 5 which transports the sample to a mixing tank in the form of an automatic turbidimeter 6.

The turbidimeter 6 comprises an open-topped vessel 7 into which the sample is introduced. the vessel is equipped with radial baffles 8, 9 and a mechanical agitator comprising one or more stirrer blades 10 mounted on a shaft 11 which is rotated by a motor 12. The lower part of the vessel 7 is narrowed and is equipped with a pair of windows 13. Light from a light source assembly 14 is directed at the right hand one of these windows and is arranged to pass through the slurry within the turbidimeter before exiting through the left hand window and into a light detector 15. The light source includes a lamp 14a and a suitable optical filter 14b which defines the frequency of the light.

The light detector 15 generates an electrical signal indicative of the optical transmission, and hence of the concentration of the slurry in the turbidimeter. This signal is passed to an electronic controller 16 which operates a valve 17 to control the flow of dilution water flowing along a line 18 to the vessel 7. In practice, the concentration of the slurry depends to a certain extent on factors other than the optical trasmission of the slurry, for example, the specific surface area of the sample. However, for a given sample, the concentration of the slurry in the vessel 7 can be automatically and accurately controlled, and preset to the level necessary to carry out the subsequent sedimentation test.

In order that the contents of the vessel 7 may be emptied, a drain valve 19 is provided whereby the contents of the vessel 7 may be pumped out by an electric pump 20. After emptying, the vessel 7 may be flushed out with clean water entering via a line 21 and automatically controlled by a valve 22. The flushing water flows into a rotating dispensing device 23 to effectively flush all the interior surfaces of the vessel 7. The full sequence of these operations will be explained later.

A facility for manual insertion of samples into the vessel is also included by means of a hopper 24 and line 25.

In the particle size analyser shown in FIG. 1, two sedimentation cells are provided, shown diagrammatically under the reference manual 26. Each cell has a hollow interior 27 into the bottom of which the slurry to be analysed is introduced from the turbidimeter via a respective line 28. The output lines 29 for slurry return to the turbidimeter to form a closed loop. When a slurry is to be tested, and has reached the appropriate concentration in the vessel 7, one of a pair of reversible flow peristaltic pumps 30 is switched on so as to pump slurry round the closed loop through the corresponding one of said sedimentation cells 26. When not in use, each pump 30 acts as a shut-off valve, thus eliminating the necessity of an independent pump and valve combination.

As explained previously, the slurry is pumped around the closed loop for a short time, until steady state conditions have been reached. The speed of pumping should be sufficient to ensure that no premature settling of the particles can occur. The flow is then stopped and the sedimentation test itself begins.

As soon as the flow is stopped the particles within the sedimentation cells begin to fall under gravity towards the bottom of the cell. Their progress is continuously monitored, from the time the flow is stopped, by means of a pair of light emitters and associated light detectors. The light emitters comprise respective fibre optics 31, 32 (four in all—two for each sedimentation cell) through which light is transmitted from a common light source 33. The light source 33 includes a good quality tungsten lamp 33a fed from a stabilized power source (not shown) and an optical filter 33b which defines the frequency of the light output which is chosen for the particular substance under analysis. Light leaves the light source 33 through a single fibre optic (for each cell) which branches to form the respective fibre optics 31, 32. The light exiting from each of the fibre optics 31, 32 travels through the sedimenting slurry in the hollow interior 27 of the sedimentation cell, and enters a corresponding light detector 34, 35 (four in all—two for each sedimentation cell).

Each of the light detectors provides an electrical output signal indicative of the amount of light transmitted through the slurry being tested at one of two different levels. These output signals are passed to a data collector 36 which provides an output signal to a dual channel X-Y recorder 27, if required, which is able to plot the variation in light transmission as a function of time for each detector. Further electronic circuitry 38 is able to process the output signal from the data collector 36 to provide the weight percent particle size distribution and the specific surface area of the sample. These results are available within minutes of the sample being collected, so the results are rapidly available for use in adjustment or control purposes on the process being monitored. It is possible to utilise the analyser as part of a closed loop control system for regulating a process in which, for example, the surface area of a finely divided solid is an important control parameter. The analyser can be installed in-plant, perform analyses in real time, and if linked through a computer, the result can be used to control automatically the critical flows in the process. The calculation principles used for calculating the above results are based on a combination of Stoke's Law and correction factors, mentioned previously, and the Beer-Lambert Law which relates the optical density of the slurry to the particle concentration. The theoretical background is well known, and will not be explained further.

It is to be understood that the other light detectors 34, 35 in the other sedimentation cell (the left hand cell in FIG. 1) are similarly connected to circuitry 36, 37 and 38, but this is not shown in order to clarify the drawing.

When the sedimentation test is completed the appropriate pump 30 is switched on in the reverse direction to pump the slurry out of the sedimentation cell 26 from the bottom, and back into the turbidimeter 6. At the same time, the drain valve 19 of the turbidimeter is opened to drain the vessel 7, as explained previously, and an appropriate one of a pair of valves 39 are opened to allow flushing water to enter a corresponding line 40 to flush out the interior 27 of the sedimentation cell 26. This flushing water enters at the top of the cell 26 through two separate branches directed at the walls of the cell to ensure very efficient washing, and is pumped out by means of the appropriate pump 30 along the corresponding line 28 to the turbidimeter 6. The level of fluid within the vessel 7 is such that it always lies below the open ends of lines 29, so that no "suck back" occurs through these lines.

It will be understood that the sequence of operation of the analyser of FIG. 1 is controlled by a central mechanical programmer or an electronic computer (not shown). A typical sequence of operations is as follows:

Assume that sedimentation tests are carried out alternately in the two cells and that a test is at present being carried out in the right hand sedimentation cell 26. During this time the pump 30 of the left hand sedimentation cell 26 is switched on to drain the slurry from the previous test (in the left hand cell) into the turbidimeter 6 where it mixes in the vessel 7 with the slurry which remains therein from the test in the right hand cell at present being carried out. The left hand cell is then flushed out as explained above. Next the vessel 7 is drained of its contents, and thence flushed out. Next a sample for the next test (to be in the left-hand cell) is taken and passed to the vessel 7 for automatic dilution. Finally the left-hand pump 30 is once more switched on to draw the diluted sample into the left hand cell for the next test. Once steady state conditions are established, the pump 30 is switched off and the next sedimentation test started in the left hand cell. Simultaneous with this, the sedimentation test in the right hand cell is halted, and the cell emptied, as described above with reference to the left-hand cell. This cycle of operations is repeated from one cell to the other, a typical time scale being 5 minutes for each sedimentation test—i.e. 12 tests per hour for a twin cell system.

Figure 2:
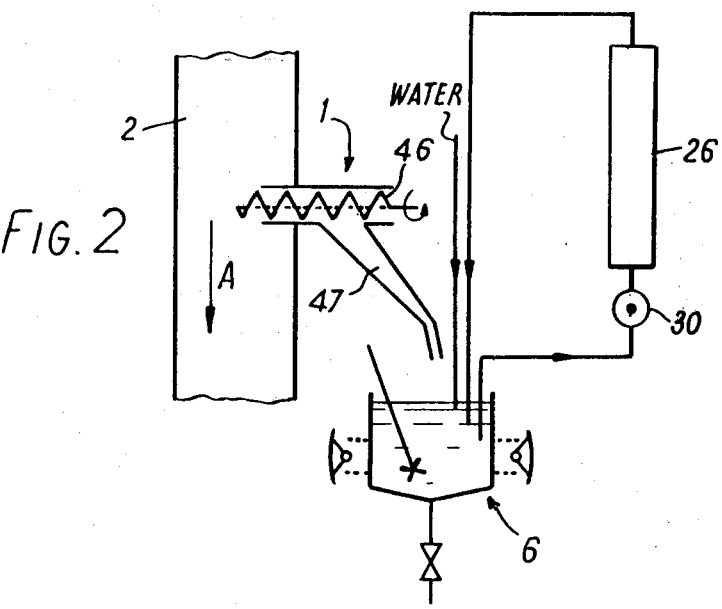
FIG. 2 shows an alternative method of obtaining samples of material from the line.

Referring now to FIG. 2 there is shown an alternative sampler for withdrawing the sample from the line 2. In this Figure, the automatic turbidimeter 6 and one sedimentation cell 26 are shown in basic outline form. It is to be understood that this sampler could be used with the analyser shown in FIG. 1.

The sampler of FIG. 2 is intended for withdrawing samples in the case where the material flowing along pipe 1 comprises solid particles in dry powder form. The sampler comprises an Archimidean screw feed 46 having an exit pipe 47 leading directly to the turbidimeter 6. The screw feed 46 extends through the wall of pipe 2 into its interior so that, upon rotation of the screw feed, a sample of powder can be transferred via the pipe 47 to the turbimeter 6. At time of sample taking, the screw is turned forward to clear the screws, then reversed to carry fresh sample out of the stream. An additional option might be the complete withdrawal of the sampler from the stream between sample taking periods.

For slurry samples a preferred type of sampler is the Isolok Model M-4KT-8 automatic iquid sampler, manufactured by Bristol Engineering Company, 210 Beaver Street, Yorkville, Ill. 60560, U.S.A. This sampler is adapted to permit automatic flushing of the sample into the turbidimeter. The type of seal rings are chosen with regard to the abrasiveness of the solid and the type of carrying liquid.

Referring now to FIGS. 3 and 4, there is shown a sedimentation cell 26 for use with the particle size analyser of FIGS. 1 and 2. The sedimentation cell 26 comprises a closed rectangular cell constructed from clear plexiglass panels. The two narrower sides 48, 49 of the cell are equipped with the light emitters 31, 32 and light detectors 34, 35 respectively. The bottom panel 50 of the cell is provided with a slurry inlet port 51 which leads to a respective pump 30 and line 28 (both not shown), while the top panel 52 of the cell is provided with six uniformly distributed slurry outlet ports 53 which ae commoned to form a respective line 29. This arrangement avoids trapping of air bubbles at the top of the cell. The line 40 for flushing water splits into two angled branches 54, 55 which terminate at the sides of the cells. This latter arrangement ensures that flushing water is directed down the walls of the cell and gives very efficient flushing. The inside surface of the bottom panel 50 is spherical in shape since this has been found to improve mixing of the slurry and to prevent premature settling of particles.

Two plate glass panels 56, and 57 are embedded in the two narrow sides 48, 49 so as to lie flush with the inside surface of the respective side, as shown. The purpose of these panels is to provide good optical surfaces. The fibre optics 31, 32 terminate on the exterior surface of the panel 56 while the light detectors 34, 35 are mounted on the panel 57. It has been found that this arrangement significantly reduces interface problems which occur at the ends of the fibre optics and at the light detectors. In addition, the fact that the glass is flat minimizes distortion problems associated with the more conventional circular section cells. Also, glass of the finest optical quality can be used without significant increase in cost.

It will be seen that the design of the cell is such that air can not be trapped at the top of the cell during flow through, or subsequent analysis. The presence of air results in a liquid/air interface at the top of the cell which can cause multiple reflections. Also, this feature enables the upper fibre optic 31 to terminate at the highest possible level in the cell. The advantage of this is that it allows a measure of the finest (and hence slowest settling) particles within a reasonably short time lapse after the beginning of the analysis. In the particular design shown, the distance between the termination of the fibre optic 31 and the top of the cell is 1.1 cm, and this has allowed determination of the six micrometer point on the size distribution curve within five minutes. Other dimensions in this same cell, given by way of example, are: distance between termination of top and bottom fibre optics: 22 cms; distance between internal surfaces of narrow sides 48, 49: 4 cm; total volume of hollow interior 27 of cell: 320cc.

The whole cell is enclosed in a light-proof box (not shown) having a light-proof door. It is eseential that the cell be shielded from all external light otherwise erratic signals are obtained. The light proof door can be used to visually monitor operaton of the cell, and to ensure that flushing has been completed after analysis. Of course, while recording, it is necessary to have the door closed to prevent stray light from reaching the detectors.

Figure 5:
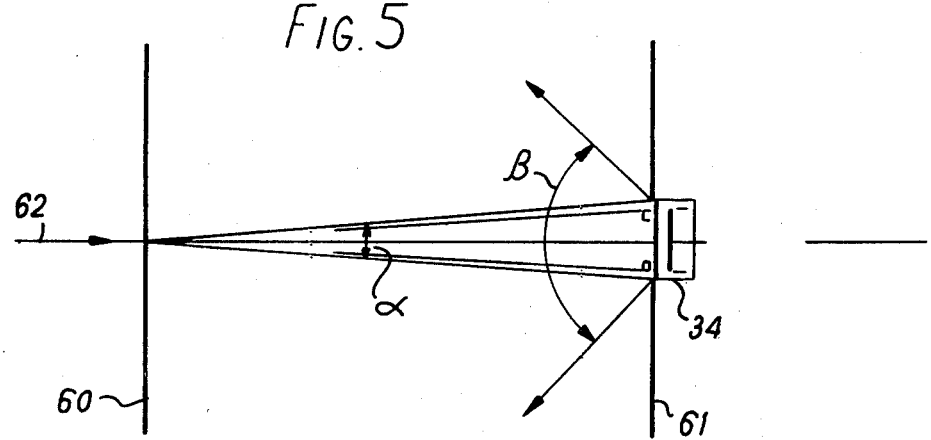
FIG. 5 is a diagram illustrating the optical arrangement of the sedimentation cell of FIG. 3.

The optical arrangement of the sedimentation cell is shown in more detail in FIG. 5 to which reference will now be made. Although described in relation to the upper fibre optic 31 and its light detector 34, it is to be understood that the same situatin exists with regard to the bottom fibre optic 32 and its detector 35.

The inside surfaces of the glass panels 56, 57 are shown under references 60 and 61 respectively, and the incident light beam from the end of fibre optic 31 is shown under reference 62. The exit of the fibre optic is shielded by a small disk (not shown) in which is formed a small slit through which the light is emitted. The size of the slit is adjusted to give a beam of light just larger than the photo-sensitive surface of the detector 34 at the point of impingement on the surface 61. The light diverges, of course, after leaving the collimator at the surface 60 and, with the cell dimensions quoted above, a beam of light subtending a vertical angle ($a_v$) of 3° and horizontal angle ($a_h$) of 6° has been found suitable. These angles can be modified according to the position of the fibre optic and detector relative to the top of the sedimentation cell. The subtended angle $\beta$ of the detector 34 is relatively large—about 90° in one example—which reduces light scattering effects.

The effect of the relatively large beam of light in the present apparatus results in a number of advantages:
1. There is compensation for the light lost be scattering from particles within the beam.
2. The output electrical noise resulting from individual large particles as they pass through the beam is greatly reduced. The noise to signal ratio can be reduced to 1/100.
3. The large area of impingement on the surface 61 means that the whole of the light sensitive area of the detector 34 can be utilised, and a high electrical output signal results. This higher voltage permits more reliable transmission over long distances, such as would be necessary if the electronic processing circuitry were remote from the analyser itself.
4. The degree of critical alignment of the optics is reduced, resulting in a more consistently improved detector output signal. By the same token, sensitivity to vibration is also reduced.
5. Because part of the information is derived from each of the detectors 34, 35, it is desirable that they have a perfectly matched gain response. This may be achieved by filling the cell with pure water and adjusting the gain for each detector to give the same output signal. For continuous operation, it is necessary to maintain this matching at somewhat better than 2% and, with the present arrangement, it has been found possible to maintain matching of the two detectors 34, 35 for relatively long periods, for example 24 hours, without adjustment.

The manner in which the information from the detectors 34, 35 is manipulated will now be described with particular reference to FIG. 6 which shows an example of the output signals from the detectors, as displayed on a dual channel X-Y recorder.

The two channels of the recorder are utilised to record the separate signals from the two detectors, the output signal from the upper detector 34 being curve A, and the output signal from the lower detector 35 being curve B. The tiny irregular fluctuations in the two curves are the result of noise, mainly optical noise due to the passage of individual large particles through the light beam shown in FIG. 5.

Figure 6:
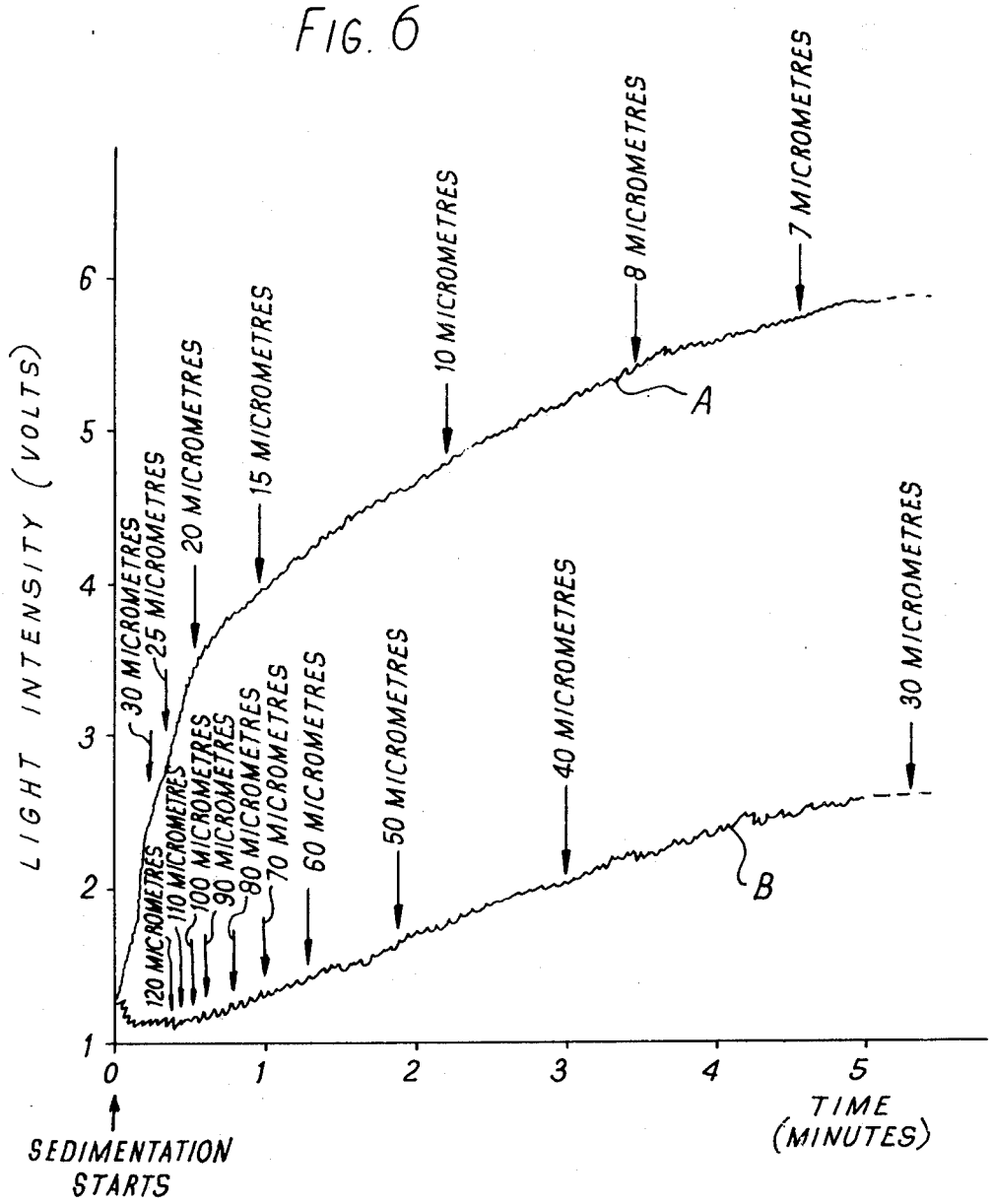
FIG. 6 is a graph showing an example of the output signals received from light detectors in the sedimentation cell of FIG. 3.

The graph of FIG. 6 illustrates the output signals of the two detectors from the time that sedimentation begins, for a period of five minutes. In practice a wait of 2 to 3 seconds after the end of slurry circulation is desirable before readings are begun, in order to permit the inherent liquid turbulence to disappear. These curves may be used directly without the circuitry 38 for control purposes by comparing them with those from previously analysed materials.

It will be noticed that there is a much more rapid increase in light transmission for the upper detector 34 than for the lower one. This is due to the fact that the settling distance for the upper detector is very short (only 1.1 cm in the example quoted above), so that the larger particles (which settle faster) pass the detector very quickly, giving rise to a relatively low concentration at this level shortly after the commencement of sedimentation. The particle size range covered by each detector is a function of their position below the surface and the time allowed for sedimentation.

With the dimensions quoted previously, and a maximum sedimentation period of about 5 minutes, the application of Stoke's Law and appropriate corrections to an alumina trihydrate sample settling in water, permits the determination of particles having a Stokes diameter of from 7 to 30 micrometers by the top detector 34 and from 30 to 120 micrometers by the bottom one. A combination of the two curves A and B allows the range 7 to 120 micrometers to be covered in a period of 5 minutes.

The 30 micrometer point, common to the two detectors, one at the end of the sedimentation period for the lower detector 35 and the other at the beginning of the sedimentation period for the upper detector 34, provides a means of checking the proper operation of the sedimentation cell and its otical system. Stoke's law predicts that, because of the time-distance interrelationship, at given points, for a given particle size, the optical density must be the same, but at different times. That is, if say at the lower detector 35, the 30 micrometer point is calculated to be reached in five minutes, and at the upper detector 34 the same point is reached in 15 seconds then, at those times, the light transmission must be the same. If they actually are then all the parameters involved in the calculation probably have been correctly determined.

The method and apparatus described above may be used to analyse a wide variety of materials which will tolerate mixing with a liquid, for example, metal oxides, air entrained dust, pigments and for specific application in the field of crystallisation, catalysis, flotation extraction or transformation processes. The instrument provides a *complete* size distribution curve, rather than a small number of discrete points on the curve. Without a complete size distribution curve which takes into account the fine particles, measuring 10 microns or less, an accurate measurement of specific surface area cannot be made. It will be appreciated that, under many practical circumstances, since the fine particles have a higher specific area than the coarse particles, they (the fine particles) account for a considerable proportion of the surface area, and it is therefore important to be able to detect such fine particles.

We claim:

1. A particle size analyser comprising a sequential sampler for periodically collecting a sample of a material to be analysed flowing along a line, a mixing tank for separately and sequentially receiving said samples, said mixing tank having means for automatically diluting each samle to a predetermined concentration, a sedimentation cell in which analysis of each individual sample by sedimentation is performed, a first fluid flow line leading from the mixing tank to the bottom of the sedimentation cell, and a second fluid flow line leading from the top of the sedimentation cell to the mixing tank, and means, including a pump, for separately and successively transferring a diluted sample from the mixing tank around a closed loop including the sedimentation cell and its fluid flow lines and for draining each sample from the sedimentation cell when the analysis of that sample is complete.

2. A particle size analyser as claimed in claim 1 wherein a plurality of said sedimentation cells are provided, each sedimentation cell having a respective pump, and wherein the analyser further comprises control means acting on said pumps to control the sequence of operation of the analyser.

3. A particle size analyser as claimed in claim 2 wherein each pump is situated in a respective first flow line.

4. A particle size analyser as claimed in claim 2 wherein the pumps are of the reversable type and are operable, in order to fill their respective sedimentation cell, to pump the diluted sample round a respective closed loop from the mixing tank, through said first flow line, back into the mixing tank until steady state conditions are reached; and, in order to empty their respective sedimentation cell, to pump the sample through the respective first line back to the mixing tank.

5. A particle size analyser as claimed in claim 2 further comprising means for flushing out each sedimentation cell after each analysis in that cell has been completed.

6. A particle size analyser as claimed in claim 5 wherein said flushing comprises a respective third flow line leading from a supply of flushing water to the top of each sedimentation cell; and wherein, in order to flush out a sedimentation cell, an appropriate one of said pumps is actuated to allow water to pass through the sedimentation cell from said water supply.

7. A particle size analyser as claimed in claim 1 wherein the mixing tank includes means for measuring the concentration of fluid therein, and valve means, under the control of said measuring means, for controlling the flow of diluent to the mixing tank.

8. A particle size analyser as claimed in claim 7 wherein the measuring means comprises a light source positioned to direct light through the diluted sample in the mixing tank, a light detector positioned to receive the light passed through the diluted sample and an electronic controller connected to the light detector, and operable to operate a valve to shut off the supply of diluent to the mixing tank when a predetermined optical transmission, corresponding to said predetermined concentration, is reached.

9. A particle size analyser as claimed in claim 2 wherein each sedimentation cell comprises a sealed lighttight vessel in which the analysis is carried out, a plurality of spaced light emitters arranged along the side of the vessel and operable to direct light through the interior of the vessel, and for each light emitter, a corresponding light detector arranged to receive light from its light emitter through the interior of the vessel.

10. A particle size analyser as claimed in claim 9 wherein the light emitters comprise a plurality of light guides, all receiving light from a common source.

11. A particle size analyser as claimed in claim 10 wherein the light guides are fibre optics.

12. A particle size analyser as claimed in claim 9 wherein the sedimentation cell is rectangular in horizontal section, and the light emitters and light detectors are positioned on respective opposite parallel sides.

13. A particle size analyser as claimed in claim 12 wherein the interior surface of each of said opposite parallel sides is lined with a respective glass panel, and wherein the light guides terminate on the exterior surface of their respective glass panel.

14. A particle size analyser as claimed in claim 9 wherein the upper part of the vessel is shaped and vented so as to prevent air being trapped at the top of the vessel during analysis.

15. A particle size analyser as claimed in claim 14 wherein the top wall of the vessel is formed with a plurality of passageways opening into the top wall of the vessel, which passageways are angled upwards to meet and form a common fluid flow line for the sample.

16. A particle size analyser as claimed in claim 9 wherein the bottom interior surface of the vessel is spherical in shape, and has a fluid flow passageway opening into it at substantially its centre point.

17. A particle size analyser as claimed in claim 9 wherein at least one of the walls of the vessel is made from transparent material, and the vessel is enclosed in a light-proof box having a light-proof door positioned such that the interior of the cell can be monitored visually.

18. A particle size analyser as claimed in claim 9 wherein each light emitter is covered by a respective disc of opaque material, each disc having a slit formed therein to allow light through, the size of said slit being such as to cause the light beam impinging on the corresponding light detector to cover an area just larger than the light sensitive surface of the detector.

19. A particle size analyser as claimed in claim 1 wherein the sequential sampler comprises an Archimidean screw feed enclosed in a pipe extending into the interior of the line carrying material to be analysed in powder form.

20. A particle size analyser as claimed in claim 19 wherein the screw feed is reversable to clean off the screw once the sample has been taken.

21. A method of automatically effecting particle size analysis on material flowing along a line, said method comprising the steps of periodically collecting a sample of the material to be analysed, separately and sequentially diluting each said sample to a predetermined concentration in a mixing tank, pumping the diluted samples from the mixing tank round a loop including a sedimentation cell and back into the tank until steady-state conditions are reached, then halting the flow and carrying out a sedimentation analysis on that portion of the sample within the sedimentation cell at that moment, and draining each samle when its analysis is complete, and wherein the period between the collection of each successive sample is never shorter than the sedimentation analysis time for the sample.

22. A method as claimed in claim 21 wherein the sample is diluted by introducing the sample into a vessel, adding a suitable diluent to said vessel whilst continually monitoring the concentration of the sample in the diluent and, when said predetermined concentraton has been reached, shutting off the supply of diluent to the vessel.

23. A method as claimed in claim 21 including the further step of passing flushing liquid through the sedimentation cell after each analysis has been completed.

24. A method as claimed in claim 23 for use with apparatus having two sedimentation cells, wherein the analyses are carried out in the two cells alternately and wherein, during the analysis in one cell, the following steps are carried out: the draining and flushing of the other cell; the collection of the next sample to be analysed; the dilution of this next sample to the predetermined concentration; and the transfer of the diluted sample to said other cell.

* * * * *

UNITED STATES PATENT AND TRADEMARK OFFICE
CERTIFICATE OF CORRECTION

PATENT NO. : 4,178,796
DATED : December 18, 1979
INVENTOR(S) : James D. Zwicker et al.

It is certified that error appears in the above-identified patent and that said Letters Patent are hereby corrected as shown below:

Abstract, sixth line, "then" should read --thence-- .

Col. 3, line 60, after the period (.), "the vessel" should read --The vessel-- .

Col. 4, line 31, "manual" should read --numeral-- ;

Col. 6, line 30, "iquid" should read --liquid-- .

Col. 7, line 35, "situatin" should read --situation-- .

Col. 8, line 66, "otical" should read --optical-- .

Col. 11, line 21, "samle" should read --sample-- .

Signed and Sealed this

Sixteenth Day of November 1982

[SEAL]

Attest:

GERALD J. MOSSINGHOFF

*Attesting Officer*  *Commissioner of Patents and Trademarks*